United States Patent [19]

Feuston et al.

[11] Patent Number: 5,510,392

[45] Date of Patent: Apr. 23, 1996

[54] POLYALPHA OLEFINS FOR FOOD AND PHARMACEUTICAL APPLICATIONS

[75] Inventors: Maureen H. Feuston, Griggstown; Choudari Kommineni, Pennington, both of N.J.; Lawrence K. Low, Yardley, Pa.; Carl R. Mackerer, Pennington, N.J.

[73] Assignee: Mobil Oil Corporation, Fairfax, Va.

[21] Appl. No.: 242,991

[22] Filed: May 16, 1994

Related U.S. Application Data

[63] Continuation of Ser. No. 101,796, Aug. 3, 1993, abandoned, which is a continuation of Ser. No. 802,960, Dec. 5, 1991, abandoned.

[51] Int. Cl.[6] .................................................. A61K 47/30
[52] U.S. Cl. ......................................................... 514/772.3
[58] Field of Search ........................... 424/78.02, 78.03, 424/78.04, 78.05, 78.06, 78.07, 78.08; 514/762, 772.3, 789; 426/390, 442

[56] References Cited

U.S. PATENT DOCUMENTS

| | | | |
|---|---|---|---|
| 2,500,166 | 3/1950 | Seger et al. | 260/688.1 |
| 2,937,129 | 5/1960 | Garwood | 208/18 |
| 3,149,178 | 9/1964 | Hamilton et al. | 260/683.9 |
| 3,382,291 | 5/1968 | Brennan | 260/683.15 |
| 3,574,827 | 4/1971 | Beerbower | 514/762 |
| 3,725,498 | 4/1973 | Brennan | 260/683.15 |
| 4,508,746 | 4/1985 | Hamm | 426/601 |
| 4,582,927 | 4/1986 | Fulcher | 560/201 |
| 4,849,242 | 7/1989 | Kershner | 426/601 |
| 4,915,974 | 4/1990 | D'Amelia et al. | 426/611 |
| 4,959,465 | 9/1990 | Klemann et al. | 536/115 |
| 4,983,413 | 1/1991 | Meyer et al. | 426/589 |

OTHER PUBLICATIONS

R. D. Galli et al. A New Synthetic Food Grade White Oil Jun., 1982 pp. 365–372.

*Primary Examiner*—Raymond Henley, III
*Attorney, Agent, or Firm*—A. J. McKillop; M. D. Keen

[57] ABSTRACT

A synthetic hydrocarbon-based material for direct use in foods and pharmaceuticals which includes a hydrogenated oligomer of an alpha olefin having 5 to 20 carbon atoms.

11 Claims, No Drawings

POLYALPHA OLEFINS FOR FOOD AND PHARMACEUTICAL APPLICATIONS

CROSS-REFERENCE TO RELATED APPLICATIONS

This application is a continuation of application Ser. No. 08/101,796, filed 3 Aug. 1993, now abandoned, which is a continuation of application Ser. No. 07/802,960, filed 5 Dec. 1991, now abandoned.

FIELD OF THE INVENTION

The present invention relates generally to synthetic hydrocarbon materials suitable for use in foods and food processing, and pharmaceuticals and, more particularly, to polyalpha olefin-based materials suitable for use as substitutes for white mineral hydrocarbons in food and pharmaceutical applications.

BACKGROUND OF THE INVENTION

In recent years, governmental agencies involved in the regulation of foods and food additives have begun to reassess the potential risk to human health arising from the use of food additives and food machinery lubricants of petroleum origin. In February 1989, the United Kingdom Ministry of Agriculture, Fisheries and Food recommended a ban on virtually all direct food applications of mineral hydrocarbons, including white mineral oils. The United Kingdom decision was based in large part upon toxicological findings reported recently with white oils in rats by industry. Concern over the health safety of white oils indicates a need to examine alternative hydrocarbon materials such as synthetic polyalpha olefins as suitable non-toxic substitutes.

In the United States all food grade oils must meet the exacting requirements of the Food and Drug Administration (FDA). Lower viscosity grades, those up to 36.8 centistokes at 40° C., are covered by U.S. National Formulary specifications, and the more viscous grades, above 38.1 centistokes at 40° C., by the U.S. Pharmacopoeia. The latter grades closely correspond to the product designated as "liquid paraffin" by the British Pharmacopoeia (BP), although the BP limits viscosity to 64 centistokes, minimum, at 40° C. The more viscous grade is also sometimes referred to as "medicinal liquid paraffin" by virtue of its use as a mild laxative. As can be appreciated, when employed for this purpose, the product must be of the highest quality and purity. A major use for food grade oils, also known as "food grade white oils" is in the lubrication of machines in which the lubricant may come in contact with foodstuffs. Other white oils, known to those skilled in the art as "technical white oils" do not require the same high level of refining necessary to meet pharmacopoeia requirements.

Petroleum-based white mineral oils are highly refined, water-white products made from lubricating oil distillates. These oils are complex mixtures of saturated hydrocarbons including straight chain, branched, ring structures and molecules containing all three configurations. White mineral oils typically have carbon numbers in the $C_{15}$ through $C_{30}$ range. The relative number of saturated ring structures and straight or branched chain structures will determine whether the oil is characterized as naphthenic or paraffinic in nature. White mineral oils are obtained from the intensive treatment of a petroleum fraction with sulfuric acid or oleum, by hydrogenation, or by a combination of sulfuric acid treatment and hydrogenation. The petroleum fraction is obtained by atmospheric and vacuum distillation to isolate the desired boiling range and viscosity and then solvent treated and dewaxed to remove polar compounds, aromatics and waxes.

Two FDA regulations govern the use of white oil and mineral oils as food grade lubricants:

21 CFR 172.878 Specifications for qualification as a white mineral oil; and

21 CFR 178.3620 Specifications for white oils for applications involving incidental food contact.

21 CFR 172.878 includes specifications for ultraviolet (UV) light absorbance, readily carbonizable substances and sulfur compounds. 21 CFR 172.878 specifies 15 uses or intended uses for white mineral oils. The FDA-approved uses are: 1) as a release agent binder or lubricant in or on capsules and tablets containing flavoring, spices and the like intended for addition to food; 2) as a release agent binder or lubricant in or on capsules and tablets for special dietary use; 3) as a float on fermentation fluids in the manufacture of vinegar and wine; 4) as a defoamer in food; 5) in bakery products, as a release agent and lubricant; 6) in dehydrated fruits and vegetables, as a release agent; 7) in egg whites, as a release agent; 8) on raw fruits and vegetables, as a protective coating; 9) in frozen meat, as a component of a hot- melt coating; 10) as a protective float on brine used in the curing of pickles; 11) in molding starch used in the manufacture of confectionary; 12) as a release agent, binder, and lubricant in the manufacture of yeast; 13) as an antidusting agent in sorbic acid for food use; 14) as a release agent and as a sealing and polishing agent in the manufacture of confectionary; and, 15) as a dust control agent for wheat, corn, soybean, barley, rice, rye, oats and sorghum. Where stated limits are given by the FDA for the above intended uses, never is the white oil percentage permitted to exceed 0.6%.

Findings from recent industry conducted toxicity studies in rats have raised some health concerns [P. Watts, Mineral hydrocarbons in food—a ban?, BIBRA Bulletin, 28: 59–65, (1989)]. Repeated administration of conventional white oils in the diet (over 90 days) leads to the accumulation of oil droplets in the lymph nodes, liver, spleen and other target tissues in the animals. At high doses, this is accompanied by granuloma formation which is considered to be toxicologically important. Hematological and clinical chemistry abnormalities were also observed in these studies which are indicative of probable adverse health effects. While many other animal studies have not produced similar effects and there have been only rare indications of adverse effects in humans despite the many years in which mineral oils have been used in food and medicinal preparations (e.g., laxatives), the use of such petroleum-based products is expected to come under continued scrutiny, with further recommendation for banning anticipated.

There exists a need to consider alternatives to white mineral hydrocarbon lubricants for use in food and pharmaceutical applications. It is known within the field of engine lubrication that certain synthetic liquids exhibit properties that are superior, from a standpoint of lubrication, to those exhibited by white oils. Hydrogenated oligomers of 6–12 carbon atom alpha olefins, as described in U.S. Pat. Nos. 3,382,291, 3,149,178 and 3,725,498 represent such a class of synthetic liquids.

In addition to possessing desirable lubricant characteristics, hydrogenated polyalpha olefin materials may offer an advantage over conventional white oils in another manner. Because of their polymeric nature and high molecular weight, polyalpha olefin materials are expected to be poorly absorbed when ingested orally. The non-absorbability of hydrogenated polyalpha olefins diminishes the likelihood of accumulation in the tissues and therefore reduces the chance of adverse effects (e.g., granuloma formation) in the tissues, thus leading to a safer non-toxic product. The notion of 'nonabsorable' polymeric food additives has been documented in the literature [J. P. Brown and T. M. Parkinson, Nonabsorable food additives through polymeric design, Drug Metabolism Reviews, 16:389–422(1985)] and represents a recent approach towards developing safer food substances. There exists a need to apply this concept toward petroleum derived lubricants such as synthetic hydrogenated polyalpha olefins.

There remains a need for synthetic hydrocarbon materials such as hydrogenated polyalpha olefins which are not readily absorbed in mammals and which are suitable for direct use in foods and pharmaceuticals and which can serve as suitable safe alternatives to conventional white mineral hydrocarbons in such applications.

SUMMARY OF THE INVENTION

In accordance with the present invention there is provided a synthetic hydrocarbon-based material for direct use in foods and pharmaceuticals, comprising a hydrogenated oligomer of an alpha olefin having 5 to 20 carbon atoms. Also provided is a process for producing a synthetic hydrocarbon-based material for direct use in foods and pharmaceuticals, comprising the steps of: (a) polymerizing an alpha olefin having 5 to 20 carbon atoms; (b) distilling the polymerized alpha olefin prepared in step (a), thereby obtaining a fraction containing dimer and a residual fraction essentially free from dimer; and (c) saturating the residual fraction produced in step (b) by hydrogenation. Also provided is a method for preparing a food or pharmaceutical for mammalian consumption, comprising the step of adding a synthetic hydrocarbon-based material which includes a hydrogenated oligomer of an alpha olefin having 5 to 20 carbon atoms.

In view therefore, it is an object of the present invention to provide a synthetic hydrocarbon-based oil for direct use in foods.

It is another object of the present invention to provide a synthetic hydrocarbon-based oil for use in pharmaceuticals.

It is a further object of the present invention to provide a synthetic hydrocarbon-based oil which can be used as a food additive.

It is yet another object of this invention to provide a synthetic oil substitute for white mineral and vegetable oils.

It is yet a further object of the present invention to provide a method for producing a synthetic hydrocarbon-based oil for direct use in foods and pharmaceuticals.

It is still yet another object of the present invention to provide a method for preparing a food or pharmaceutical for mammalian consumption.

Other objects and the several advantages will become apparent to those skilled in the art upon a reading of the specification and the claims appended thereto.

DETAILED DESCRIPTION OF THE INVENTION

The compositions of this invention are synthetic hydrocarbon materials which display the physical properties of petroleum-based mineral oils and waxes. They are liquid or solid at room temperature, depending upon molecular weight and structure. Preferred are those hydrogenated oligomers described in U. S. Pat. Nos. 3,382,291, 3,149,178 and 3,725,498, the contents of which are hereby incorporated by reference for all that they disclose. When reference is made herein to the terms "polymerized normal alpha-monoolefin" or "polyalpha olefin (PAO)" refers to synthetic materials made by polymerizing normal alpha-monoolefins ($C_5$ to $C_{20}$) either thermally or catalytically in the presence of a di-tertiary alkyl peroxide or a Friedel-Crafts catalyst, including boron trifluoride and aluminum chloride, under mild conditions. Of the group of polyalpha olefins, particular preference is accorded to the hydrogenated oligomers of 1-decene, 1-octene and mixtures thereof, with 1-decene being the most preferred monomer. It is known that polymers made in the presence of a di-tertiary alkyl peroxide are the substantial equivalent of thermally polymerized olefins. When Friedel-Crafts catalysts are used, polymerization conditions are to be relatively mild.

In order to produce the synthetic hydrocarbon-based oils for direct use in foods and pharmaceuticals of this invention, the selection of the normal alpha-monoolefin monomer is important. As indicated, the monomer which is particularly preferred is 1-decene although mixtures of normal alpha-monoolefins having between about 5 and about 20 carbon atoms can be used, although it is preferred that the mean value of the olefin chain length is about 10 carbon atoms.

Thermally polymerized olefins utilizable herein are described in U.S. Pat. No. 2,500,166, the contents of which are hereby incorporated for such details. The polymerization is carried out generally at temperatures varying between about 500° F. and about 750° F. for periods of time varying between about 20 hours and about one hour. The olefin reactants are normal alpha-monoolefins having between 6 carbon atoms and 12 carbon atoms per molecule. The utilizable olefins are, for example, 1-hexene, 1-octene, 1-nonene, 1-decene, and 1-dodecene. The olefin reactant can be substantially pure normal alpha-monoolefins or mixtures of normal alpha-monoolefins having between six and twelve carbon atoms.

The synthetic materials produced by polymerizing normal alpha-monoolefins in the presence of di-tertiary alkyl peroxide catalyst are described in U.S. Pat. No. 2,937,129, the contents of which are hereby incorporated by reference. Again, the olefin reactant is a normal alpha-monoolefin, or a mixture thereof, preferably containing between 6 and 12 carbon atoms, inclusive, per molecule. Examples are 1-heptene, 1-octene, 1-decene, and 1-dodecene. The catalyst is a di-tertiary alkyl peroxide, preferably di-tertiary lower alkyl peroxides. A readily-available and especially preferred catalyst is di-tertiary butyl peroxide. The amount of peroxide catalyst used is between about 0.01 and about 0.3 mole per mole of normal alpha-monoolefin reactant. The temperature employed is the activation temperature of the peroxide catalyst and varies between about 100° C. (212° F.) and about 200° C. (392° F.).

As indicated above, the polyalpha olefins utilizable in the present invention can readily be prepared in the presence of Friedel-Crafts catalysts, under relatively mild conditions. As is well known to those skilled in the art, severe operating conditions, particularly with some promoted Friedel-Crafts catalysts, induce undesirable side reactions, isomerization, resinification, etc. It is further recognized that all Friedel-Crafts catalysts are not entirely equivalent in the type of materials produced. To a great extent, the choice of catalyst and of reaction conditions can be made in order to produce synthetic hydrocarbon materials of a desired viscosity.

Polymerization of 1-decene (or its equivalent) with $AlCl_3$ catalyst at temperatures below about 70° C. produces synthetic materials having a kinematic viscosity of 25–45 centistokes at 210° F. In general, such oils are produced by gradually mixing olefin with 1–3 weight percent (based on the total olefin charge) of $AlCl_3$ over a period of 2–6 hours. A preferred procedure involves incremental addition of the olefin to a slurry of catalyst in an inert hydrocarbon, e.g., n-heptane.

Polymerization of 1-decene (or its equivalent) in the presence of $AlCl_3$ at temperatures of 100–200° C. yields materials of about 12 centistokes kinematic viscosity measured at 210° F. A feasible method of operation is to add $AlCl_3$ rapidly to olefin, permitting the temperature to rise suddenly to 150° C. or higher. Under these conditions polymerization occurs readily, to the extent that most of the olefin is consumed before the reaction mixture reaches the boiling point of decene.

In the case of $BF_3$-catalyzed polymerization, either pressure or a catalyst promoter are necessary, in order to produce high quality polyalpha olefins. Suitable promoters are $BF_3$-decanol complex, decanol, acetic acid, and acetic acid $BF_3$ complex. Generally, the polymerization is carried out at temperatures below about 60° C for a total reaction time on the order of about 2–4 hours. When $BF_3$ polymerization is carried out under pressure, a reaction time of 2–4 hours is employed. The pressure, measured in terms of $BF_3$ pressure, can vary between about 10 pounds per square inch gauge and about 500 pounds per square inch gauge or higher. In both types of $BF_3$ catalyzed polymerization of 1-decene (or its equivalent) polymer oils are produced having kinematic viscosities of about 3–6 centistokes at 210° F.

Particularly preferred in preparing the synthetic hydrocarbon materials of the present invention is the process disclosed in U.S. Pat. No. 3,382,291. The process so disclosed comprises feeding to a reaction zone a stream of alpha olefins saturated with $BF_3$ and a stream of $BF_3$ complexed in a 1:1 molar ratio with a promoter, and commingling those streams in a reaction zone under polymerization reaction conditions. The process is carried out using the usual conditions for $BF_3$-catalyzed polymerization of alpha olefins. The temperature utilized is generally below about 60° C. and preferably between about 0° C. and about 35° C. The reaction can be carried out at atmospheric pressure, but moderate pressures of from about one psig up to about 500 psig are preferred.

The alpha olefin charge can be any normally liquid alpha olefin having between 5 and about 20 carbon atoms or mixtures of such alpha olefins. Non-limiting examples of the alpha olefin charge are 1-pentane; 3-methyl-1-butene; 1-hexene; 3,3-dimethyl- 1-butene; 2,3-dimethyl-1-butene; 1-heptene; 1-octene; 1-decene; 2,3,3-trimethyl-1-pentene; 2-ethyl-1-hexene; 1-hexadecene; 1-octadecene and 1-eicosene.

The alpha olefin charge is saturated with $BF_3$, at room temperature (about 20° C.), before it is charged to the reaction zone. This can be accomplished by any means known to those skilled in the art. Thus, the alpha olefin charge can be saturated by bubbling $BF_3$ gas through an alpha olefin batch, as in a storage vessel, or it can be saturated by bubbling $BF_3$ gas through an alpha olefin charge stream as it passes through on to the reaction vessel.

As is well known, $BF_3$, per se, is a poor catalyst for polymerizing olefins, unless it is promoted with water or other substances capable of forming coordination compounds. Therefore, the alpha olefin saturated with $BF_3$ should be free of water and other impurities.

The second stream that is charged to the reactor is a 1:1 molar complex of $BF_3$ and a promoter compound. This complex, upon contacting the first stream (the alpha olefin charge) in the reactor, effects the polymerization reaction. The promoter compound used to form the $BF_3$-promoter catalyst complexes are well-known in the art. They include, by way of non-limiting examples: water; alcohols, such as octanol and 1-decanol; acids, such as acetic acid, propionic acid, and butyric acid; ethers, such as diethyl ether; acid anhydrides, such as acetic acid anhydride and succinic anhydride; esters, such as ethyl acetate and methyl propionate; and ketones and aldehydes, such as acetone and benzaldehyde.

The rate at which the first and second streams are charged to the reactor can vary widely, dependent in part upon the size of the reactor, but primarily upon the cooling capacity of the reactor. Thus the rate of addition of the streams is limited only by the ability to remove exothermic heat of polymerization, so as to maintain a predetermined polymerization temperature.

The rate of addition of the second stream ($BF_3$-promoter) relative to the rate of addition of the first stream (alpha olefin saturated by $BF_3$) is adjusted to add only a catalytic amount and to avoid any excess over the catalytic amount. This rate is conveniently expressed in terms of moles of promoter per weight unit of olefin. This rate will be between about 0.006 mole promoter and about 0.01 mole promoter per 100 grams of alpha olefin charge. Using this relative rate of addition, a uniform rate of polymerization is attained and local overheating is avoided, thus enhancing the reproducibility of process results from run to run.

The process is carried out using the usual conditions for $BF_3$-catalyzed polymerization of alpha olefins. The temperature is generally below about 60° C. and preferably between about 0° C. and about 35° C. The reaction can be carried out at atmospheric pressure, but moderate pressures of from about one psig up to about 500 psig are preferred.

After addition of the alpha olefin charge is completed, the reaction mixture is generally held at the reaction temperature for an additional period of time. This hold time will usually be between about 1 hour and about 3 hours, although higher hold times can be used. This process can also be carried out continuously by withdrawing a product stream at the rate of influent streams, as those skilled in the art will readily understand. After a stable state reaction condition is reached, the average residence time will be equal to the aforedescribed hold time, thus affording a uniform product.

Following polymerization of the alpha olefin, hydrogenation is required. It is preferred when producing the synthetic hydrocarbon materials of this invention that hydrogenated material be obtained by removing, through distillation, a fraction of the polymerized normal alpha-monoolefins containing dimer compounds. The residue so obtained is then hydrogenated to saturate the olefinic double bonds. The unsaturated dimer cut can be recycled to the polymerization step, along with fresh monomer feed. Alternatively, the same results can be obtained by first hydrogenating the polymerized olefin synthetic oil and then removing the dimer. This method, however, is often less desirable, because the dimer is now saturated and not available for recycling to the polymerization step. Thus, if there is no use for the saturated dimer, it is a loss to the process.

The present invention is further illustrated by the following non-limiting examples, which are presented for illustrative purposes only, and are not intended to limit the scope of the invention as defined by the appended claims.

EXAMPLE 1

A synthetic polyalpha olefin was produced from 1-decene in substantial accordance with the preferred $BF_3$ catalyzation process described above, distilled to remove dimer compounds produced in that polymerization process and hydrogenated. Properties typical of the hydrogenated alpha decene so produced are shown in Table 1, below.

TABLE 1

SUMMARY OF PAO PROPERTIES

| PROPERTY | VALUE |
| --- | --- |
| Relative Density | 0.828 |
| Kinematic Viscosity | |
| at 40° C., cst | 28.0 |
| at 100° C., cst | 5.2 |
| Flash Point, °C. | 232 |
| Boiling Point, °C. | 316 |
| Pour Point, °C. | −54 |
| Vapor Pressure, mm Hg @ 20° C. | 0.1 |
| Dimer Content, Wt % | 0.35 |

EXAMPLE 2

This example demonstrates that a synthetic hydrocarbon oil, produced substantially as described in Example 1, is suitable in applications in which repeated human exposure via ingestion is experienced. An evaluation of the potential toxicity of the synthetic material was conducted using Sprague-Dawley rats because of the large amount of industry experience with this strain of rat and the fact that rats are an acceptable species for predicting toxicological effects in humans. The test material was administered in the diet. The dose levels employed were selected on the basis of industry experience with white mineral oils, as well as the practical considerations concerning the amount of material that can be added to feed without affecting its palatability or stability.

Administration of the synthetic hydrogenated polyalpha olefin material occurred daily over a three-month period (90-days) with necropsies completed at the end of that period. The evaluation was conducted in accordance with the Good Laboratory Practices of EPA Standards (40 CFR Part 792) and FDA Standards (31 CFR Part 58) and in accordance with the FDA and EPA guidelines.

A summary of the experimental design is presented in Table 2. The evaluation was designed for a minimum period of 90 days. As stated above, the test material was administered in the diet.

TABLE 2

SUMMARY OF EXPERIMENTAL DESIGN

| Group Number | Treatment | PAO Conc. in Diet (ppm)+ | Initial | Number of Animals in Lab. Studies* | Necropsy |
| --- | --- | --- | --- | --- | --- |
| 1 | Control Group | 0 | 20 M, 20 F | 10 M, 10 F | All |
| 2 | PAO added to diet | 500 | 20 M, 20 F | 10 M, 10 F | All |
| 3 | PAO added to diet | 5,000 | 20 M, 20 F | 10 M, 10 F | All |
| 4 | PAO added to diet | 20,000 | 20 M, 20 F | 10 M, 10 F | All |

*Except Urinalysis - only Groups 1 & 4, the first 10 animals/sex/group.
+ppm (parts per million) or microgram PAO per gm diet feed.

Ninety male and ninety female virus-antibody-free Sprague-Dawley rats were received when they were approximately twenty-nine days of age. They were acclimated to the testing facility for twelve days prior to allocation into experimental groups. The animals were individually housed in suspended, stainless steel cages having wire mesh bottoms and fronts, and kept in air-conditioned rooms set to maintain a temperature of 68°–72° F., a relative humidity of 40–60% and a 12-hour light-dark cycle. The animals were provided with food (Purina Certified Lab Chow) and water ad libitum.

Prior to the initiation of treatment, animals were randomly assigned to different test groups to provide a statistically identical ($p<0.05$) body weight distribution. Animals considered to be unhealthy were not assigned to the groups. Any animal which became abnormal prior to the initiation of dosing was replaced with a healthy animal that was not assigned to an experimental group. After initiation of treatment, no animals were replaced.

The hydrogenated polyalpha olefin was incorporated into the diet (Purina Certified Lab Chow, #5002) at levels of 0, 500, 5,000 and 20,000 ppm. To determine if diet preparation procedures were appropriate, a trial diet was mixed at 500 and 20,000 ppm. These diets were then analyzed for homogeneity, stability and percentage of hydrogenated polyalpha olefin in the diet. The diet had to be stable for a minimum of three weeks. Subsequently, the experimental and control diets were prepared approximately one week prior to the initiation of treatment and at approximately two week intervals thereafter. Each batch of test diet was analyzed for homogeneity, stability and percentage of test material in the diet. To be acceptable for animal consumption, the concentration of test material in the diet had to be at or within 10% of the desired level. A fresh batch of diet was supplied every two weeks. Animals had continual access to the test diet except for periods of deprivation required for hematology and serum chemistry studies and necropsy.

Each animal was observed daily during the course of the study for normal or abnormal clinical signs. The parameters observed included appearance, behavior, excretory function, and discharges. Animals were checked for moribundity and mortality twice daily, at least six hours apart, on weekdays. On weekends and holidays, they were checked once.

Animals were weighed the day after receipt and prior to their release from quarantine (the latter for allocation into the experimental test groups). Animals allocated into experimental groups were weighed immediately before the initiation of treatment and approximately weekly thereafter. The body weight of each animal was measured to the nearest tenth of a gram and recorded.

The amount of feed consumed by each animal was determined three times per week. Food consumption data were not collected during the necropsy period. The food fed and the food remaining weights were measured to the nearest tenth of a gram. Food spillage was checked daily. All recoverable food spillage was weighed, the amount recorded and then discarded; these data were used in calculating the amount of food consumed. When a rat spilled food which was non-recoverable, the consumption data for that animal were excluded from data calculations for that collection interval.

The first ten animals per sex per group had blood collected prior to the initiation of treatment and during Weeks 5 and 13. Blood samples were collected from the scheduled animals in a single day. The afternoon before blood collections, food was removed from the cage of each rat. Food was returned after the collection was completed. Samples were analyzed on the same calendar day that they were collected for the following:

| | |
|---|---|
| hematocrit | red blood cell count |
| hemoglobin | white blood cell count |
| platelet count | |

Mean corpuscular volume, mean corpuscular hemoglobin and mean corpuscular hemoglobin concentration were calculated. During blood collection, a determination of red blood cell morphology and white blood cell differentials was made.

At least 1 ml of whole blood from each rat was collected, allowed to clot for approximately thirty minutes, and centrifuged to obtain the serum. Samples were analyzed for the following biochemical parameters:

| | | |
|---|---|---|
| sorbitol dehydrogenase | cholesterol | glucose |
| alanine aminotransferase | triglycerides | uric acid |
| aspartate aminotransferase | total protein | potassium |
| alkaline phosphatase | albumin (A) | calcium |
| inorganic phosphorus | urea nitrogen | chloride |
| bilirubin, total | creatinine | sodium |

Globulin (G) and A/G ratio were calculated.

All animals were examined prior to the initiation of treatment for eye abnormalities. Animals found to have eye abnormalities were not allocated into experimental groups. The eyes of the study animals were reexamined during Week 13.

During Weeks 5 and 13, freshly voided urine samples were collected and analyzed. Samples were obtained from the first ten animals per sex in Groups 1 and 4. The samples were examined visually for appearance (i.e., color and clarity), and then analyzed for the following:

| | | | |
|---|---|---|---|
| bilirubin | blood | glucose | specific gravity |
| ketone | pH | protein | urobilinogen |

All animals were euthanized with $CO_2$, exsanguinated and necropsied. Each animal had the food removed from its cage the afternoon prior to its scheduled sacrifice. All necropsies were performed using industry accepted procedures. From all animals, the following organs (where applicable) were weighed to the nearest milligram:

| | | | |
|---|---|---|---|
| adrenals | heart | ovaries | testes |
| brain | kidneys | prostate | thymus |
| epididymides | liver | spleen | uterus |

The following tissues, from the animals in Groups 1 & 4 were processed for microscopic examination according to industry accepted procedures:

| | |
|---|---|
| adrenals (both) | pancreas |
| bone and marrow (sternum) | peripheral nerve |
| brain (3 sections) | (sciatic) |
| epididymides | pituitary gland |
| esophagus | prostate and seminal |
| eye (left) and optic nerve | vesicies |
| gross lesions | salivary gland |
| heart and aorta | (submaxillary) |
| intestine, small (duodenum, jejunum and ileum) | skeletal muscle (thigh) |
| | spinal cord (cervical and |
| intestine, large (cecum, colon and rectum) | thoracic) |
| | spleen |
| kidneys (both) | stomach (glandular, |
| liver | pyloric and squamous) |
| lung (left lobe) | testes (both) |
| lymph nodes (mesenteric) | thymus (both lobes) |
| nammary gland | thyroid/parathyroid |
| ovaries (both) | trachea |
| prostrate and seminal vesicles | urinary bladder |
| salivary gland | uterus (body and horns) |

Sections for examination were stained with hematoxylin and eosin and microscopic examination performed.

Body weights, clinical signs and food jar weights were recorded, as were urinalysis results, mortality and animal husbandry data.

Quantitative data (body weights and organ weights) were analyzed by parametric methods: analysis of variance (ANOVA) and associated F-test, followed by Dunnett's test (body weights) or Tukey's multiple comparison test (organ weights), provided that there was statistical significance in ANOVA. Differences between control and treated groups were considered statistically significant only if the probability of the differences being due to chance was less than 5% ($p<0.05$).

The following summarizes the findings of the evaluation of Example 2. Repeated oral administration over 90 days of a hydrogenated polyalpha olefin, even to as high as 2% concentration in the diet, produced no mortality or clinical signs of systemic toxicity. No statistically significant differences were observed in the mean body weights between exposed and control animals.

In addition, no statistically significant differences were observed between the hematology data from the untreated and the hydrogenated polyalpha olefin-treated animals. Clinical chemistry data showed no abnormalities indicative of organ toxicity. There was no evidence of any changes in serum aspartate aminotransferase or alanine aminotransferase which would indicate adverse liver effects. Differences in albumin/globulin ratio and the globulin concentrations in serum were statistically significant ($p<0.05$) in male rats at 20,000 ppm and differences in serum inorganic phosphorus were statistically significant in female animals at 20,000 ppm. In lieu of any histopathological findings (see below), these serum chemistry findings are not considered to be biologically significant.

Food consumption was not different between control animals and animals fed the test material in their diet for 90 days. Urinalysis and ophthalmological evaluation showed no treatment-related effects.

Macroscopic examination of the organs showed no abnormalities. There was no histopathological evidence of toxicity in the organs. Microscopic examination for oil droplet formation showed no evidence of any accumulation of the test material in the tissues (e.g., liver, spleen, lymph nodes); nor was there any evidence of granulomatous reactions or macrophage infiltration in these tissues. None of the major organ systems, including the liver, kidney, lungs, lymphatic and nervous systems, showed any detectable treatment-related changes. In general, there was no statistically significant differences in the absolute or relative organ weight data attributable to exposure to hydrogenated polyalpha olefins.

In view of the fact that there were no adverse effects observed in the test animals, even when the hydrogenated polyalpha olefin was present in the diet at 2% of the total dietary intake, the materials of the present invention are suitable for use in direct contact with foodstuffs, as food additives and in pharmaceuticals where food-grade or medicinal quality mineral oils have been used historically. Due to the molecular weight of the hydrogenated polyalpha olefins disclosed hereinabove, the synthetic hydrocarbon oils of the present invention are not readily absorbable or digestible in mammals and would provide an excellent non-caloric, zero metabolic fat content substitute for vegetable oils. In addition, the fact that these materials are not readily absorbed from the gastrointestinal tract may be an important factor governing their safety.

In conclusion, hydrogenated polyalpha olefins in the diet at concentrations of 500, 5,000 and 20,000 ppm produced no detrimental health effects in animals. Feeding studies as described in Example 2 showed no clinical, hematological or histopathological evidence of adverse effects. Microscopic examination for oil droplet formation showed no evidence of accumulation of polyalpha olefin materials in tissues such as liver, spleen, lymph nodes and there was no evidence of granulomatous reactions in these tissues, which is in sharp contrast to what has been reported by the industry for some conventional white mineral oils. Thus, hydrogenated polyalpha olefin materials such as that described in Example 2 show considerable suitability as a safe and non-toxic alternative to conventional white oils for use in food and pharmaceutical applications.

EXAMPLE 3

This example demonstrates that a synthetic hydrocarbon oil, produced substantially as described in Example 1, is suitable in applications where repeated human dermal exposure is experienced.

The synthetic was applied to the skin of groups of 10 male and 10 female Sprague-Dawley rats five days/week for thirteen weeks at dose levels of 800 and 2000 mg/kg/day. The rats were fitted with cardboard collars to minimize the ingestion of applied test material, which was left uncovered on the shaved skin. The untreated controls were handled in the same manner as the test animals, except that no material was applied to their skin. Toxicity was assessed by body and organ weights, clinical signs, dermal irritation, urinalysis, clinical chemistry, gross and microscopic pathology, sperm morphology, and hematology.

TABLE 3

SUMMARY OF EXPERIMENTAL DESIGN

| Group Number | Treatment | Dose Level (mg/kg/day) | Treated | Number of Animals in Lab Studies | Necropsy |
|---|---|---|---|---|---|
| 1 | Control | 0 | 15 M, 15 F | All | All |
| 2 | PAO | 800 | 15 M, 15 F | All | All |
| 3 | PAO | 2000 | 15 M, 15 F | All | All |

Each weekday for thirteen weeks, the test substance was applied to the clipped (shaved) back of rats in the treated groups. Every animal received an amount of the test material calculated from its most recent body weight, the density of the test material, and the dose for that treatment group. The test material was administered from a syringe. Control animals were handled in the same manner, but no material was applied. Doses were based on those used in previous studies with similar materials.

| Evaluation of Toxicity | Occurrence |
|---|---|
| Clinical Signs | Daily |
| Skin Irritation | Weekly |
| Mortality | Twice Daily |
| Body Weight | Weekly |
| Laboratory Studies | Weeks 0, 5, 9, 13 |
| Hematology | All Animals |
| Serum Chemistry | All Animals |
| Urinalysis | All Animals |
| Gross Necropsy | At termination |
| Organ Weights | At termination |
| Histopathology | At termination Groups 1 and 3 |

Male rats treated with the test material at doses of 2000 mg/kg/day, gained slightly less weight than controls. At the end of the study the mean body weight of the high-dose group was 8–9% less. The basis for the decrease in weight gain in the males is not known, but this same effect has been seen in similar studies with petroleum-based oils. It could be due to less-efficient use of nutrients, an increased metabolic rate, decreased food consumption, or any combination of these. It is believed that these differences in weight are not of toxicologic importance.

The following summarizes the findings of the evaluation of Example 3. No severe effects were noted in the treated animals. Two animals died during blood collections in Week 5, presumably from anesthetic overdoses. However, no gross abnormalities were found in either animal at necropsy. No differences among the groups were found for any urinalysis parameter examined. No differences among the groups were found for any hematology parameter examined. No differences in sperm head morphology or general sperm morphology were observed between control and high-dose rats. No organs were identified as abnormal by gross observation, microscopic examination, organ weight changes, clinical observations, or serum chemistry changes. A few differences between control and treated animals were seen in serum chemistry and relative organ weights. These were judged not to represent toxicity because the magnitude of the differences was small, the organ weight ratio differences mainly reflected body weight differences, and no microscopic abnormalities were found in the tissues.

A slight flaking of the skin was seen in a few animals with a slightly higher incidence in the treated groups compared to controls, see Table 4. Males were slightly more affected than females, and there was no difference among the dose groups. No differences were seen in the skin either by gross or microscopic examination.

TABLE 4

| | Mean Skin Irritation Scores | | | | | |
|---|---|---|---|---|---|---|
| | Males | | | Females | | |
| | Group No.: | | | | | |
| | 1 | 2 | 3 | 1 | 2 | 3 |
| | (mg/kg/day): | | | | | |
| Dose | Control | 800 | 2000 | Control | 800 | 2000 |
| Erythema Grade | | | | | | |
| Day 8 | 0.0 | 0.1 | 0.1 | 0.0 | 0.1 | 0.3 |
| Day 92 | 0.0 | 0.0 | 0.1 | 0.0 | 0.0 | 0.0 |
| CDS Grade | | | | | | |

TABLE 4-continued

| | Mean Skin Irritation Scores | | | | | |
|---|---|---|---|---|---|---|
| | Males | | | Females | | |
| | Group No.: | | | | | |
| | 1 | 2 | 3 | 1 | 2 | 3 |
| | | | (mg/kg/day): | | | |
| Dose | Control | 800 | 2000 | Control | 800 | 2000 |
| Day 8 | 0.0 | 0.2 | 0.1 | 0.0 | 0.0 | 0.0 |
| Day 92 | 0.1 | 0.0 | 0.1 | 0.0 | 0.0 | 0.0 |

Erythema Scores: 0 = Normal, 1 = Barely Perceptible, 2 = Definite Redness, 3 = Moderate Redness, 4 = Severe Redness; CDS (Chronic Deterioration of Skin) Scores: 0 = Normal, 1 = flaking of skin, 2 = feels slightly stiffened and thickened, 3 = stiffness and thickening definite (visible), 4 = stiff with cracks and fissures, 5 = open sores and/or scar tissue.

As can be appreciated, Example 3 demonstrates the suitability of the synthetic hydrocarbon-based material in applications involving dermal exposure. Base oils produced from a hydrogenated oligomer of an alpha olefin having 5 to 20 carbon atoms are non-irritating and non-toxic.

Although the present invention has been described with preferred embodiments, it is to be understood that modifications and variations may be utilized without departing from the spirit and scope of this invention, as those skilled in the art will readily understand. Such modifications and variations are considered to be within the purview and scope of the amended claims.

What is claimed is:

1. In an ingestible food- or pharmaceutical-grade material for mammalian consumption by ingestion, which includes a hydrocarbon component, the improvement comprising the presence, as the hydrocarbon component, of a synthetic hydrocarbon-based material which includes a hydrogenated oligomer of an alpha olefin having 5 to 20 carbon atoms.

2. The material of claim 1, in which the alpha olefin is a normal alpha monoolefin having 6 to 12 carbon atoms.

3. The material of claim 2, in which the alpha olefin is 1-decene.

4. The material of claim 1 in which the hydrogenated oligomer is essentially free of dimer compounds.

5. The material of claim 1 in which the hydrogenated olefin oligomer is made by:

(a) polymerizing an alpha olefin having 5 to 20 carbon atoms;

(b) distilling the polymerized alpha olefin prepared in step (a), thereby obtaining a fraction containing dimer and a residual fraction essentially free from dimer; and (c) saturating the residual fraction produced in step (b) by hydrogenation.

6. The material of claim 5 in which the alpha olefin is a normal alpha monoolefin having 6 to 12 carbon atoms.

7. The material of claim 6 in which the alpha olefin is 1-decene.

8. The material of claim 5 in which the olefin is polymerized by:

(a) feeding to a reaction zone a first stream of the alpha olefin saturated with $BF_3$ and a second stream of $BF_3$ complexed in a 1:1 molar ratio, with a promoter;

(b) commingling the first and second streams in the reaction zone under polymerization reaction conditions; and (c) controlling the relative rate of addition of the first and second streams to charge between about 0.006 mole and about 0.01 mole promoter per 100 grams of alpha olefin.

9. The material of claim 8 in which the $BF_3$ and the $BF_3$ complexed with a promoter comprise the sole catalyst system.

10. The material of claim 8 in which the promoter is 1-decanol.

11. The material of claim 8 in which the alpha olefin is 1-decene.

* * * * *